(12) United States Patent
Tada

(10) Patent No.: US 7,065,240 B2
(45) Date of Patent: Jun. 20, 2006

(54) RETICLE INSPECTION APPARATUS

(75) Inventor: Akifumi Tada, Tokyo (JP)

(73) Assignee: NEC Corporation, Tokyo (JP)

( * ) Notice: Subject to any disclaimer, the term of this patent is extended or adjusted under 35 U.S.C. 154(b) by 730 days.

(21) Appl. No.: 10/224,559

(22) Filed: Aug. 21, 2002

(65) Prior Publication Data

US 2003/0044058 A1 Mar. 6, 2003

(30) Foreign Application Priority Data

Aug. 28, 2001 (JP) .............................. 2001-258532

(51) Int. Cl.
*G06K 9/00* (2006.01)
(52) U.S. Cl. .............. 382/145; 250/201.2; 250/559.41; 356/237.1; 356/239.8; 356/614; 382/144
(58) Field of Classification Search ............. 250/201.2, 250/559.41; 356/237.1, 239.8, 614; 382/144, 382/145
See application file for complete search history.

(56) References Cited

U.S. PATENT DOCUMENTS

| | | | | |
|---|---|---|---|---|
| 5,098,191 | A | * | 3/1992 | Noguchi et al. ............. 356/394 |
| 5,539,514 | A | * | 7/1996 | Shishido et al. .......... 356/237.4 |
| 6,052,478 | A | * | 4/2000 | Wihl et al. ................... 382/145 |
| 6,141,038 | A | * | 10/2000 | Young et al. .................. 348/87 |
| 6,169,603 | B1 | * | 1/2001 | Takayama .................... 356/500 |
| 6,466,315 | B1 | * | 10/2002 | Karpol et al. ............. 356/237.4 |
| 6,541,747 | B1 | * | 4/2003 | Kikuchi et al. ........... 250/201.2 |
| 6,549,290 | B1 | * | 4/2003 | Miura et al. ................. 356/614 |
| 6,797,975 | B1 | * | 9/2004 | Nishiyama et al. ..... 250/559.04 |
| 6,937,754 | B1 | * | 8/2005 | Eguchi ........................ 382/145 |

FOREIGN PATENT DOCUMENTS

| | | |
|---|---|---|
| JP | 10-30988 | 2/1998 |
| JP | 10-260366 | 9/1998 |
| JP | 11-306554 | 11/1999 |

OTHER PUBLICATIONS

Copy of Japanese Office Action dated Jul. 20, 2004 (and English translation of relevant portion).

* cited by examiner

*Primary Examiner*—Sanjiv Shah
*Assistant Examiner*—Gregory Desire
(74) *Attorney, Agent, or Firm*—Dickstein, Shapiro, Morin & Oshinsky, LLP.

(57) ABSTRACT

A reticle inspection apparatus for detecting defects on a reticle 16 includes an image data generator 42 for generating image data of the reticle 16, a definition analyzer 44 for analyzing definition of image from the image data, a definition judge device 45 for judging whether or not the definition of image is within a predetermined reference range and a sensor position regulating stage 34 for correcting a position of a position sensor 33 when the definition of image is out of the reference range. The reticle inspection apparatus constructed as mentioned is reliable and capable of automatically diagnosing an error of an auto-focusing function of the reticle inspection apparatus due to deformation, etc., of the reticle inspection apparatus.

3 Claims, 6 Drawing Sheets

FIG. 6A
FIG. 6B
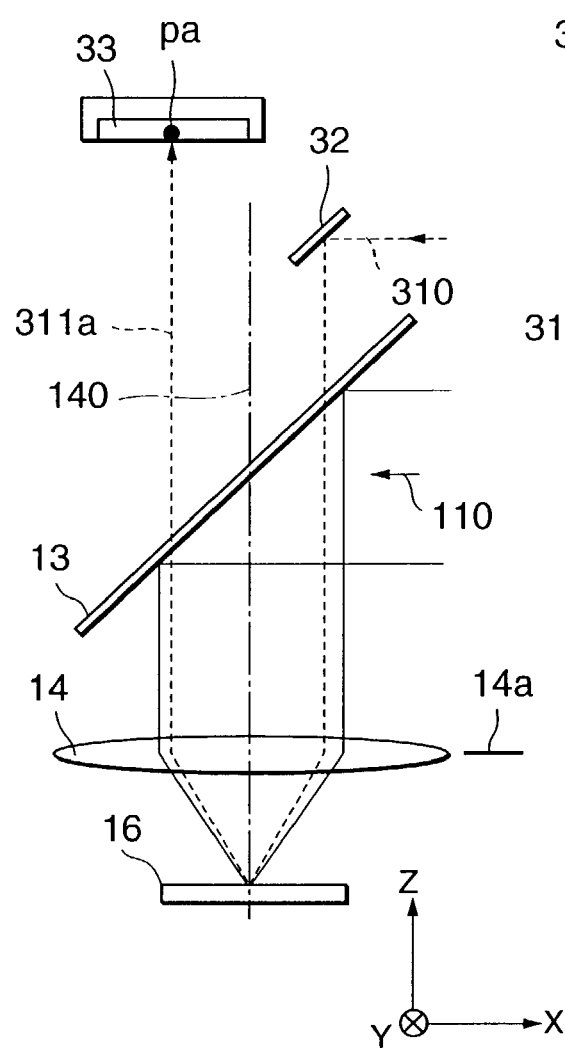
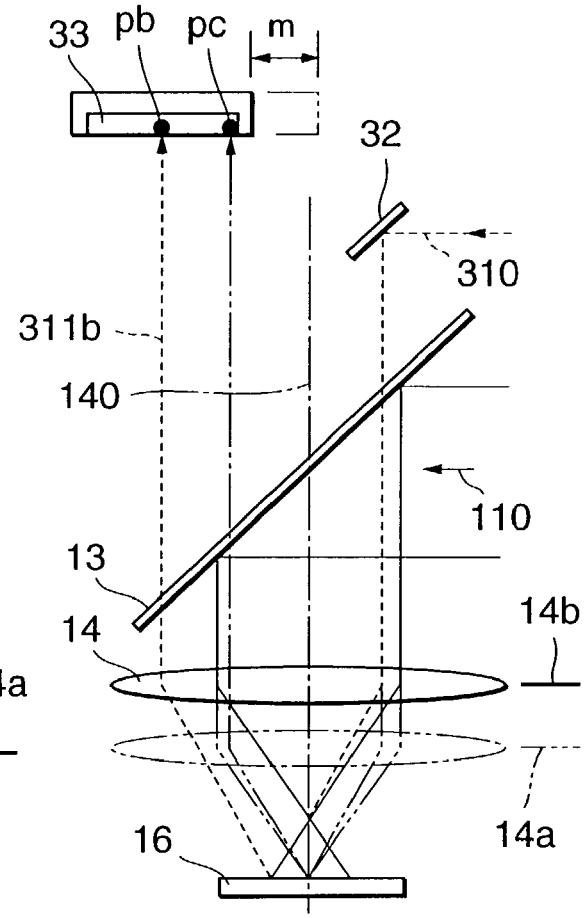

RETICLE INSPECTION APPARATUS

BACKGROUND OF THE INVENTION

1. Field of the Invention

The present invention relates to a reticle inspection apparatus for detecting defects on a reticle and, in particular, the present invention relates to a reticle inspection apparatus including an auto-focusing device and having a self diagnosis function for diagnosing the reticle inspection apparatus on error occurring in the auto-focusing device and an automatic correction function for automatically correcting the error of the auto-focusing device on the basis of the diagnosis.

2. Description of the Prior Art

It has been usual that a conventional reticle inspection apparatus for detecting defects on a reticle by irradiating the reticle with laser light includes an auto-focusing device. The auto-focusing device is used to make a focus point of the laser light coincident with a detecting position of the reticle by measuring a distance between an objective lens of an auto-focusing optical system of the reticle inspection apparatus and a detecting surface of the reticle and controlling a position of the objective lens such that the distance between the objective lens and the detecting surface is maintained optimally. In general, such auto-focusing device is operated according to the astigmatic method or the knife-edge method in which a detecting light for detecting defects of the reticle is used in an auto-focusing purpose or the oblique-incidence method in which a light source dedicated to the auto-focusing is used, etc.

Such auto-focusing device has been used in various devices such as cameras, microscopes and semiconductor exposing devices, etc. In the reticle inspection apparatus, the regulation accuracy of auto-focusing operation in the level of 0.1 μm is required due to the increased NA (Numerical Aperture) of a detecting optical system of the auto-focusing device by the recent miniaturization of semiconductor device.

In order to accommodate with this request, U.S. Pat. No. 6,052,478 proposes an auto-focusing device including two optical systems and operating according to the astigmatic method. In the proposed auto-focusing device, an inspection light reflected from an object to be inspected is divided to two inspection light portions, which are incident on the respective optical systems, and the auto-focusing operation is regulated by comparing configurations of beam spots in the respective optical systems. Further, JP H10-030988A and JP H11-306554A propose auto-focusing devices operating according to the oblique-incidence method, respectively.

Among these prior arts methods, the oblique-incidence method will be described. FIG. 1 illustrates a conventional auto-focusing device operating according the oblique-incidence method. As shown in FIG. 1, a conventional reticle inspection apparatus includes a detecting optical system 10, an auto-focusing optical system 30b and a controller system 40b. Incidentally, in FIG. 1, a lateral direction on the drawing sheet is set to an X-direction (rightward being +X and leftward being −X), a vertical direction is set to a Z-direction (upward being +Z and downward being −Z) and a normal direction to the drawing sheet is set to a Y-direction (going direction being +Y and coming direction being −Y).

In the detecting optical system 10, an inspection laser light source 11 emitting inspection laser light 110 to direction −X is provided and, along an optical path of the inspection laser light 110, a telescope 12 for expanding the laser light 110, a mirror 13 for reflecting the laser light 110 to direction −Z, an objective lens 14 for condensing the laser light 110 reflected by the mirror 13 and an X-Y stage 17 mounting a reticle 16 to be inspected and moving the reticle in the X and Y directions are provided in the order.

Subsequent to the reticle 16, a lens 18 for condensing an inspection light 111, which is the inspection laser light 110 transmitted through the reticle 16, and an inspection light sensor 19 for measuring intensity of the inspection laser light 111 condensed by the lens 18 are provided. Further, a beam splitter 20 is provided between the mirror 13 and the objective lens 14, for transmitting the inspection laser light 111 reflected by the mirror 13 to the reticle 16 through the objective lens 14 and deflecting the inspection laser light 111 reflected by the reticle 16 as an inspection laser light 112. Subsequent to the beam splitter 20, a lens 21 for condensing the inspection laser light 112 deflected by the beam splitter 20 and a light sensor 22 for measuring intensity of the inspection laser light 112 condensed by the lens 21 are provided. The objective lens 14 is supported by a regulation mechanism 15. The regulation mechanism 15 regulates a distance between the objective lens 14 and the reticle 16 by regulating height or level of the objective lens 14 with respect to the reticle 16.

In the auto-focusing optical system 30b, a He—Ne laser light source 31 for emitting auto-focusing laser light 310 in direction −X is provided and, subsequent to the He—Ne laser light source 31, a mirror 32 for reflecting the auto-focusing laser light 310 is provided. The mirror 32 is arranged such that the auto-focusing laser light 310 is reflected thereby to direction −Z, travels along a path, which is in parallel to an optical axis 140 of the objective lens 14 and is separated from the optical axis 140, and then is incident obliquely to the reticle 16 through the objective lens 14. Further, a position sensor 33 for detecting an incident position of an auto-focusing laser light 311, which is the auto-focusing laser light 310 incident on and reflected by the reticle 16, is provided.

The controller system 40b includes an image data generator 42 inputted with output signals of the inspection light sensor 19 and the inspection light sensor 22 and coordinates data of the X-Y table 17, for generating an image data of a pattern of the reticle 16 on the basis of measured data of light intensities of the transmitted inspection light 111 and the reflected inspection light 112, a defect extractor 43 responsive to the image data from the image data generator 42, for extracting defect of the reticle 16 on the basis of the image data, an X-Y stage controller 46 connected to the image data generator 42 and the X-Y table 17 for controlling an operation of the X-Y table 17 and outputting the coordinates data of the X-Y table 17 to the image data generator 42, an auto-focusing (AF) controller 48 for arithmetically operating a signal from the position sensor 33 and a lens position controller 49 for regulating a position of the objective lens 14 by actuating the regulation mechanism 15 on the basis of a signal inputted from the auto-focusing controller 48. In addition thereto, the controller system 40b includes an input/output device 41 connected to the image data generator 42 and the defect extractor 43, for instructing various devices in the controller system 40b and outputting an inspected result is provided. Incidentally, the auto-focusing device in this reticle inspection apparatus is constructed with the auto-focusing optical system 30b, the auto-focusing controller 48 and the lens position controller 49.

An operation of the conventional reticle inspection apparatus shown in FIG. 1 will be described. First, the inspection laser light 110 emitted from the inspection laser light source 11 in direction −X is expanded by the telescope 12 and, after reflected to direction −Z by the mirror 13, is condensed by the objective lens 14 and irradiates the reticle 16 mounted on the X-Y stage 17. In this case, the reticle 16 is irradiated with the inspection laser light 110 having substantially minimum beam spot. By moving the X-Y stage 17 mounting the reticle 16 thereon in X and Y directions according to the signal from the X-Y stage controller 46, the irradiating spot of the inspection laser light 110 on the reticle 16 is moved on the reticle 16 relatively. The X-Y stage controller 46 outputs the coordinates data of the X-Y stage 17 to the image data generator 42. The inspection laser light 111, which is the inspection laser light 110 transmitted through the reticle 16, is condensed on the inspection sensor 19 by the lens 18 and its intensity is measured by the inspection light sensor 19. On the other hand, the inspection laser light 112, which is the inspection laser light 110 reflected by the reticle 16, is deflected to direction −X by the beam splitter 20 and condensed on the inspection light sensor 22 by the lens 21. The inspection light sensor 22 measures intensity thereof.

The image data generator 42 generates the image data of the reticle 16 by processing the intensity signals from the inspection light sensor 19 and the inspection light sensor 22 and the coordinates data from the X-Y stage controller 46 and outputs the image data to the defect extractor 43. The defect extractor 43 detects defect of the reticle 16 by comparing the image data with design data, etc., of the reticle 16.

On the other hand, the auto-focusing laser light 310 emitted by the He—Ne laser 31 in direction −X is reflected by the mirror 32 to direction −Z and passes along the optical path, which is parallel to the optical axis 140 of the objective lens 14 and is separated therefrom. Thereafter, the auto-focusing laser beam 310 is transmitted through the mirror 13 and the beam splitter 20, refracted at the objective lens 14 and incident on the reticle 16 obliquely. The auto-focusing laser light 310 is reflected by the reticle 16 as the reflected auto-focusing light 311. The reflected auto-focusing light 311 is refracted by the objective lens 14 again to direction +Z, transmitted through the beam splitter 20 and the mirror 13 and incident on the position sensor 33. The position sensor 33 detects the incident position of the reflected auto-focusing light 311.

In the reticle inspection apparatus shown in FIG. 1, a relation between the incident position of the reflected auto-focusing light 311 on the position sensor 33 and height of the objective lens 14 is determined simply. That is, when height or level of the objective lens 14 is optimal and the inspection laser light 110 is focused on the reticle 16, the auto-focusing light 311 is incident on the position sensor 33 at a predetermined position thereof. On the contrary, when the position of the reticle 16 is sifted in direction +Z or the position of the objective lens 14 is shifted in direction −Z, that is, when the positions of the reticle 16 and/or the objective lens 14 is shifted in mutually approaching direction, the incident position of the reflected auto-focusing light 311 on the position sensor 33 is shifted in direction +X. When the position of the reticle 16 is shifted in direction −Z or the position of the objective lens 14 is shifted in direction +Z, that is, the reticle 16 and/or the objective lens 14 is shifted in mutually separating direction, the incident position of the reflected auto-focusing light 311 on the position sensor 33 is shifted in direction −X.

A signal outputted by the position sensor 33 and indicative of the incident position of the reflected auto-focusing light 311 on the position sensor 33 is processed in the auto-focusing controller 48 to generate a signal necessary to remove the shift. The latter signal is outputted to the lens position controller 49 for regulating the height of the objective lens. The lens position controller 49 operates the regulation mechanism 15 according to the input signal to regulate the height or level of the objective lens 14 such that the incident position of the reflected auto-focusing light 311 on the position sensor 33 becomes the predetermined position. Therefore, the objective lens 14 is regulated such that the distance between the objective lens 14 and the reticle 16 is always kept constant. As a result, the spot diameter of the inspection laser light 110 becomes always minimum in the vicinity of the inspection position of the reticle 16.

However, there are problems in the described conventional technique, which will be described. There may be a case where, when the reticle inspection apparatus is used for a long period of time, the inspection apparatus itself is gradually deformed due to temperature variation and/or atmospheric pressure variation in an environment in which the inspection apparatus is installed. Further, gradual deformation of a structure of the inspection apparatus may also occur by the weight of the inspection apparatus itself. With such deformation of the reticle inspection apparatus, the positional relation between the inspection optical system 10 and the auto-focusing optical system 30b, shown in FIG. 1, and positional relations between the respective constructive components of the inspection optical system 10 and the auto-focusing optical system 30b are gradually changed from the initially set relations. As a result, the auto-focusing function of the reticle inspection apparatus is gradually degraded, so that there is provided an off-focus problem of the image data of the reticle and the reticle inspection cannot be performed normally.

In the case where the inspection of the reticle 16 cannot be performed, it is necessary to judge whether or not there is any error in the auto-focusing function of the reticle inspection apparatus. In order to perform such judgement, it is necessary to check the reticle inspection apparatus itself in detail. Therefore, if the reticle inspection apparatus is installed in a factory on the side of a user, there is another problem that engineers of a manufacturer of the reticle inspection apparatus must visit the user factory and perform the detailed checks of the reticle inspection apparatus therein. This is troublesome and time consuming.

SUMMARY OF THE INVENTION

The present invention was made in view of these problems and has an object to provide a reliable reticle inspection apparatus capable of automatically diagnosing error of an auto-focusing function thereof due to deformation, etc., thereof.

The reticle inspection apparatus of the present invention includes an inspection laser light source, an objective lens, an image generator, an auto-focusing laser light source, a position sensor, a lens position regulator, and a definition evaluating device for analyzing definition of a reticle image and evaluating whether or not the definition is within a tolerable range. The inspection laser light source is used for emitting a laser light for inspection. The objective lens is used for condensing the inspection laser light and irradiating a reticle with the condensed light. The image generator is used for generating an image of the reticle on the basis of the inspection laser light reflected by the reticle and the inspection laser light transmitted through the reticle and detecting defects on the reticle. The auto-focusing laser light source is used for emitting auto-focusing laser light to the reticle through the objective lens in a direction oblique to an optical axis of the objective lens. The position sensor is used for receiving the auto-focusing laser light reflected by the reticle through the objective lens and detecting an incident position of the reflected auto-focusing laser light thereon. The lens position regulator is used for making a focal position of the objective lens coincident with the inspection position on the reticle by calculating a distance between the objective lens and the reticle on the basis of a result of detection of the position sensor and regulating a position of the objective lens with respect to the reticle.

In the present invention, defect on the reticle is detected by emitting the inspection laser light from the inspection laser light source, condensing the inspection laser light by the objective lens, irradiating the reticle with the condensed laser light and generating the image of the reticle by the image generator on the basis of the inspection laser light reflected by the reticle and the inspection laser light transmitted through the reticle. Besides, the auto-focusing laser light emitted from the auto-focusing laser light source is refracted by the objective lens and irradiates the reticle obliquely. The irradiating laser light incident on the reticle obliquely is reflected by the reticle and is refracted by the objective lens again to the position sensor. There is a constant relation between an incident position of the laser light on the reticle and a distance between the reticle and the objective lens. Therefore, the position sensor detects the incident position of the auto-focusing laser light and the lens position regulator regulates height of the objective lens on the basis of the detected incident position such that the distance between the reticle and the objective lens is kept constant, so that the focal point of the objective lens can be set always on the reticle. The definition evaluating device evaluates definition of the reticle image to diagnose the auto-focusing device on whether or not it functions normally. Incidentally, the auto-focusing device is constructed with the auto-focusing laser light source, the position sensor and the lens position regulator of the objective lens. With this construction of the reticle inspection apparatus, when an error occurs in the auto-focusing device due to deformation of some parts thereof and definition of the reticle image is degraded, it is possible to automatically evaluate the degree of degradation of definition and to diagnose on whether or not the auto-focusing device is operating normally. As a result, reliability of the reticle inspection can be improved.

Further, the reticle inspection apparatus according to the present invention preferably comprises a position sensor regulator for regulating the position of the position sensor. When definition of the reticle image is degraded out of the tolerable range, it is possible to regulate the position of the position sensor by the position sensor regulator. As a result, it is possible to recover definition in the tolerable range.

It is preferable to regulate the position of the objective lens by the lens position regulator on the basis of a result of evaluation obtained by the definition evaluating device. In such case, when the definition of the reticle image is degraded out of the tolerable range, it is possible to correct the error of the auto-focusing function and recover the image definition in the tolerable range, without necessity of the position sensor regulator for regulating the position of the position sensor.

Therefore, when the positional relations of the respective constitutional components of the auto-focusing device are changed from the initial settings due to changes of structural components such as casings of the device with passage of a long time, it is possible, at an initial stage of the change of the positional relations, to avoid a situation that the reticle inspection apparatus can not perform a desired inspection, by automatically diagnosing the fact and correcting it. Thus, it becomes possible to provide a reticle inspection apparatus capable of stably operable for a long period of time.

BRIEF DESCRIPTION OF THE DRAWINGS

FIG. 6A illustrates an automatic correcting operation for automatically correcting a relation between an incident position of an auto-focusing laser light reflected by the reticle on a position sensor and a position of an objective lens with respect to the reticle, showing a case where the relation is an initially regulated state and the reticle inspection apparatus is normal;

FIG. 6B is the same as FIG. 6A except that the relation shown in FIG. 6A is shifted due to long time structural deformation of the inspection apparatus and definition of the image data becomes out of a tolerable range;

DETAILED DESCRIPTION OF THE PREFERRED EMBODIMENTS

Figure 1:
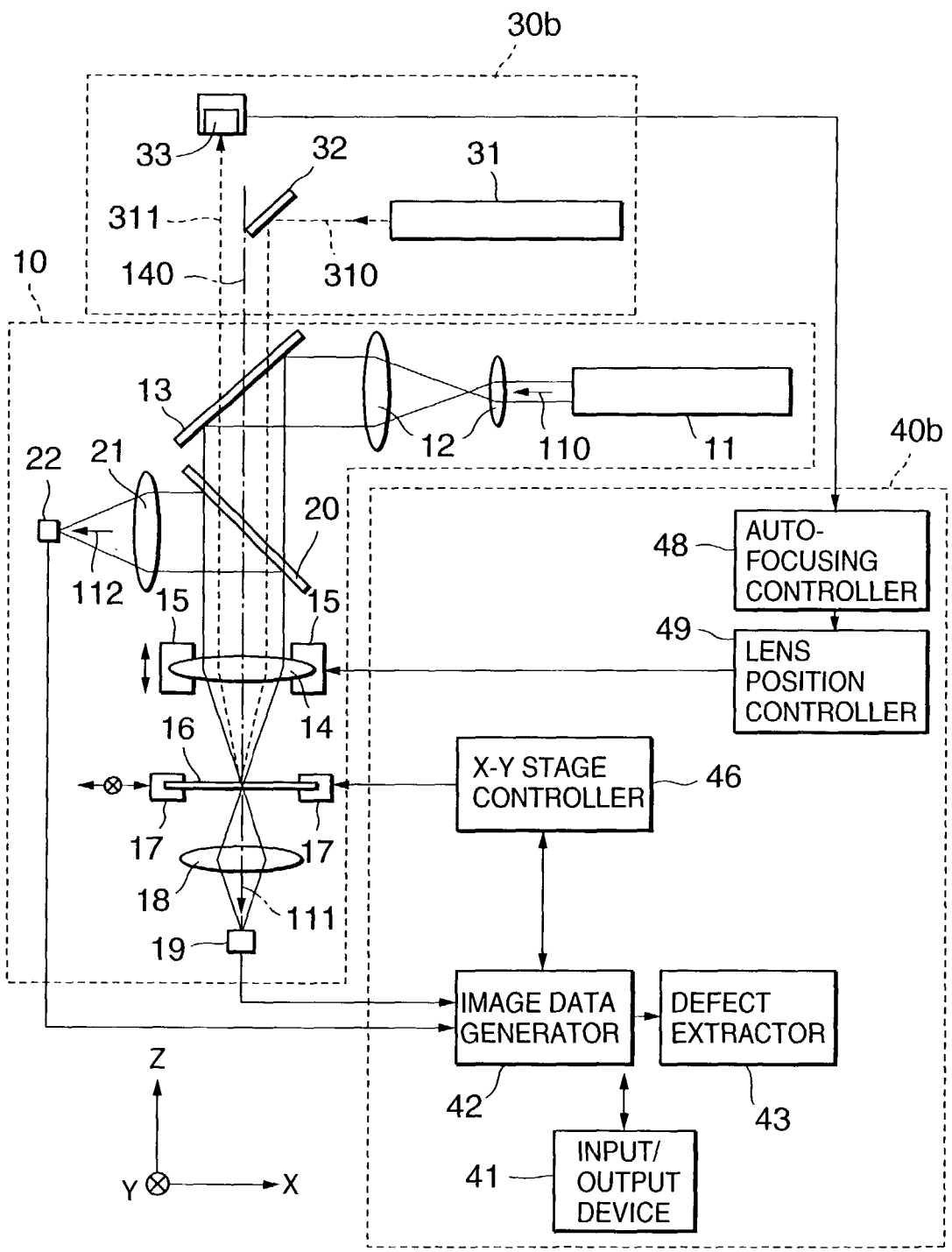
FIG. 1 is a block diagram showing a conventional auto-focusing device operable according to the oblique-incidence method.
Figure 2:
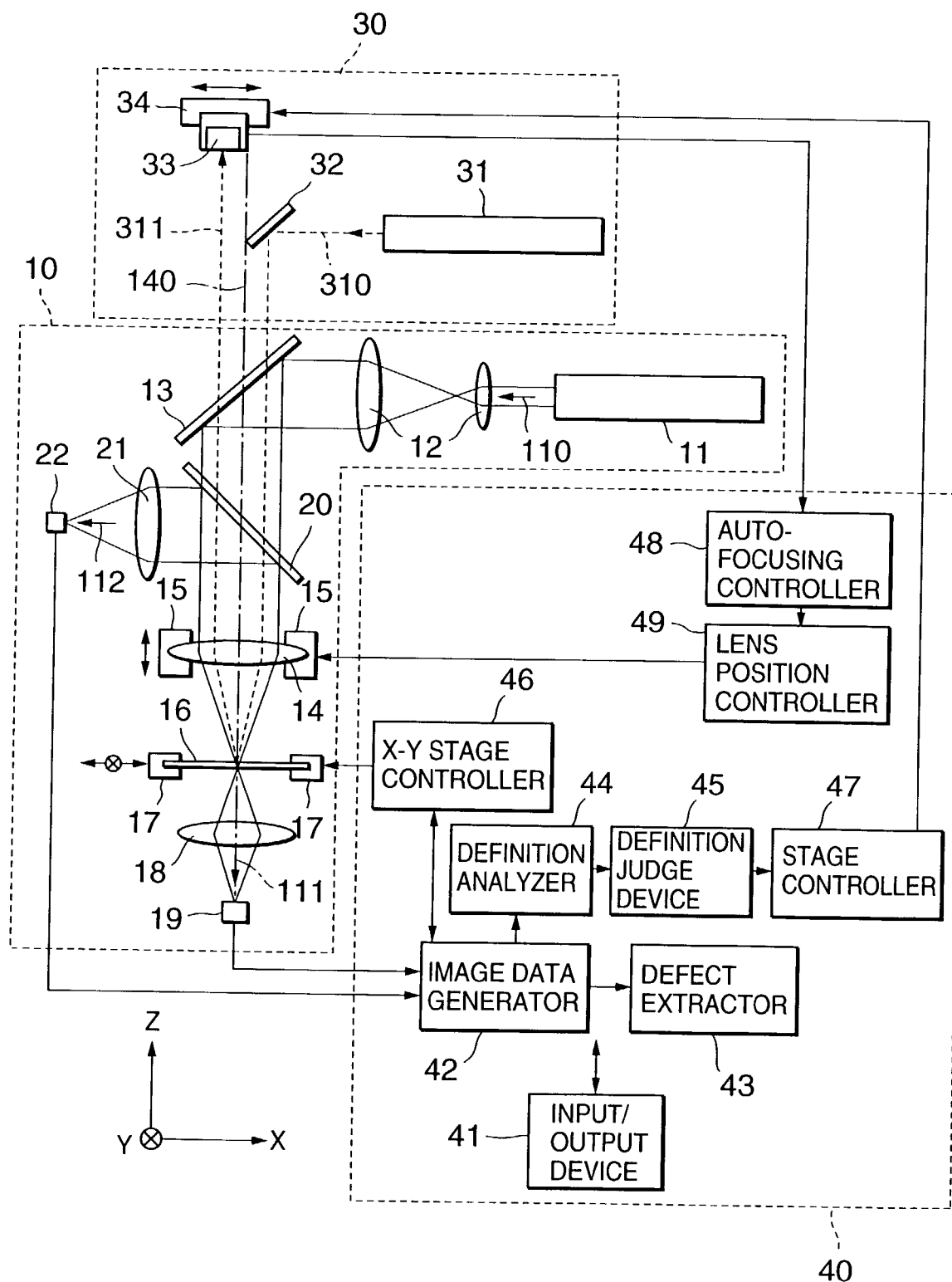
FIG. 2 is a block diagram showing a reticle inspection apparatus according to a first embodiment of the present invention.

Embodiments of the present invention will be described with reference to the accompanying drawings. FIG. 2 illustrates a reticle inspection apparatus according to a first embodiment of the present invention. In FIG. 2, components, which are the same as those shown in FIG. 1, are depicted by the same numerals as those used in FIG. 1, respectively. As shown in FIG. 2, the reticle inspection apparatus of this embodiment is constructed with an inspection optical system 10, an auto-focusing optical system 30 and a controller system 40. Incidentally, in FIG. 2, a lateral direction on the drawing sheet is set to an X-direction (rightward being +X and leftward being −X), a vertical direction is set to a Z-direction (upward being +Z and downward being −Z) and a normal direction to the drawing sheet is set to a Y-direction (going direction being +Y and coming direction being −Y), as in FIG. 1.

The inspection optical system 10 includes an inspection laser light source 11 emitting inspection laser light 110 in direction −X and further includes, along an optical path of the inspection laser light 110, a telescope 12 for expanding the laser light 110, a mirror 13 for reflecting the laser light 110 to direction −Z, an objective lens 14 for condensing the laser light 110 reflected by the mirror 13 and an X-Y stage 17 mounting a reticle 16 to be inspected and moving the latter in X and Y directions in the order. An optical axis 140 of the objective lens 14 is in parallel to a vertical direction, that is, the Z direction. A surface of the X-Y stage 17 on which the reticle 16 is mounted is perpendicular to the Z direction.

Figure 3:
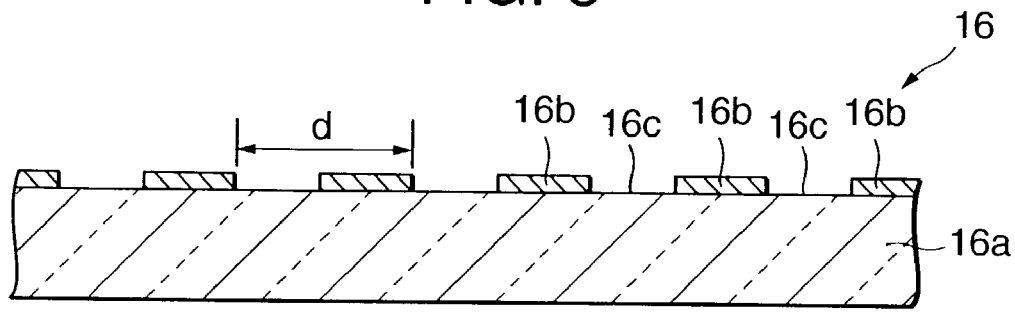
FIG. 3 is a cross sectional view of a line-and-space pattern of a reticle 16.

FIG. 3 is a cross section of an example of a reticle 16 and a line-and-space pattern is formed on the reticle 16. As shown in FIG. 3, the reticle 16 is formed by equidistantly forming rectangular light shield portions, that is, lines, 16b on a reticle substrate 16a formed of a transparent glass material. An arranging direction of the rectangular light shield portions 16b on the reticle substrate 16a is orthogonal to a longitudinal direction of the rectangular light shield portion 16b. A portion of the reticle substrate 16a between adjacent rectangular light shield portions 16b becomes a transparent portion, that is, space, 16c. Thus, the line-and-space pattern is formed on the reticle substrate 16a. The light shield portions (lines) 16b and the transparent portions (spaces) 16c are alternately arranged with constant period d.

Subsequent to the reticle 16, a lens 18 for condensing the inspection laser light 110, which is transmitted through the reticle 16 as a transmitted inspection light 111, and a transmitted inspection light sensor 19 for measuring intensity of the transmitted inspection light 111 condensed by the lens 18 are provided. Further, between the mirror 13 and the objective lens 14, a beam splitter 20 for transmitting the inspection laser light 110 reflected by the mirror 13 and deflecting the inspection laser light 110, which is reflected by the reticle 16 as a reflected inspection light 112, to direction −X, a lens 21 for condensing the reflected inspection light 112 deflected by the beam splitter 20 and a reflected light sensor 22 for measuring intensity of the reflected inspection light 112 condensed by the lens 21 are provided. Further, a lens position regulator 15 for supporting the objective lens 14 and regulating a distance between the objective lens 14 and the reticle 16 by regulating a position of the objective lens 14 with respect to the reticle 16 in the Z direction is provided.

In the auto-focusing optical system 30, a He—Ne laser light source 31 for emitting auto-focusing laser light 310 in direction −X is provided and, subsequent to the He—Ne laser light source 31, a mirror 32 for reflecting the auto-focusing laser light 310 is provided. The mirror 32 is arranged such that the auto-focusing laser light 310 is reflected thereby to direction −Z, travels along a path, which is in parallel to an optical axis 140 of the objective lens 14 and is separated from the optical axis 140, and then is incident obliquely to the reticle 16 through the objective lens 14. Further, a position sensor 33 for detecting an incident position of the auto-focusing laser light 310, which is reflected by the reticle 16 as an auto-focusing laser light 311, thereon and a sensor position regulating stage 34 for regulating a position of the position sensor 33 in the X direction are provided. The auto-focusing optical system 30 is provided above the inspection optical system 10 and includes the sensor position regulating stage 34, the position sensor 33, the mirror 32, the mirror 13, the beam splitter 20, the objective lens 14, the reticle 16, the X-Y stage 17, the lens 18 and the transmitted inspection light sensor 19 arranged along the optical axis 140 of the objective lens 14 in the order. However, the mirror 32, the sensor position regulating stage 34 and the position sensor 33 among them are arranged in positions slightly deviated from the optical axis 140. The He—Ne laser light source 31 is arranged in direction +X when looked from the mirror 32, the telescope 12 and the inspection laser light source 11 are arranged in direction +X when looked from the mirror 13 and the lens 21 and the reflected light inspection sensor 22 are arranged in direction −X when looked from the beam splitter 20.

The image data generator 42 of the controller system 40 is inputted with output signals of the transmitted inspection light sensor 19 and the reflected light inspection sensor 22 and an output signal of an X-Y stage controller 46, which is to be described later, generates the image data of the pattern of the reticle 16 on the basis of the measured intensities of the transmitted inspection light 111 and the reflected inspection light 112 and the coordinates data of the reticle 16 and measures the light intensity distribution of the image data.

Figure 4:
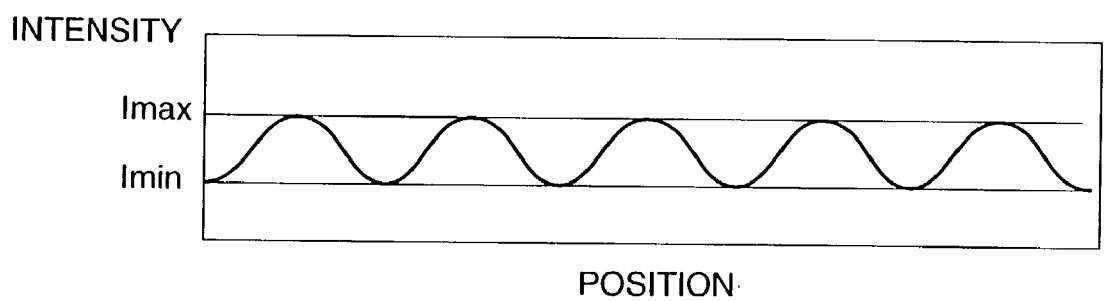
FIG. 4 is a graph showing light intensity distribution of an image data of the reticle, with a position in an orientation direction of the line-and-space pattern on a reticle substrate being in abscissa and light intensity of an image obtained by detecting the line-and-space pattern by the reticle inspection apparatus according to the first embodiment being in ordinate.

FIG. 4 is a graph showing light intensity distribution of an image data of the reticle 16, with a position in an arranging direction of the line-and-space pattern on a reticle substrate 16a being in abscissa and light intensity of an image obtained by detecting the line-and-space pattern by the reticle inspection apparatus according to the first embodiment being in ordinate. When the image data generator 42 generates an image data of the line-and-space pattern of the reticle shown in, for example, FIG. 3, light intensity distribution corresponding thereto becomes as shown in FIG. 4.

The defect extractor 43 of the controller system 40 is inputted with the image data from the image data generator 42 and extracts defect of the reticle 16 from the image data. Further, the X-Y stage controller 46 is connected to the image data generator 42 and the X-Y table 17 to control the operation of the X-Y table 17 and to output the coordinates data of the X-Y stage 17 to the image data generator 42. Further, the auto-focusing controller 48 arithmetically operates the output signal of the position sensor 33 by which the reflected auto-focusing light 311 is detected. A lens position controller 49 for regulating a position of the objective lens with respect to the reticle is inputted with an output signal of the auto-focusing controller 48 and regulates the position of the objective lens 14 by controlling the operation of the lens position regulator 15 on the basis of the thus inputted signal.

A definition analyzer 44 is inputted with the light intensity distribution of the image data outputted from the image data generator 42 (see FIG. 4) and analyzes the definition of the image of the reticle on the basis of this light intensity distribution. The definition analyzer 44 will be described in detail. The definition analyzer 44 obtains maximum light intensity Imax and minimum light intensity Imin from the light intensity distribution and calculates MTF (Modulation Transfer Function) according to the following equation (1). Further, it obtains the period d shown in FIG. 3 and calculates the number of lines per 1 mm (Line (mm$^{-1}$)) according to the following equation (2).

$$MTF=(Imax-Imin)/(Imax+Imin) \qquad \text{(Equation (1))}$$

$$Line\ (mm^{-1})=1/d\ (mm) \qquad \text{(Equation (2))}$$

Figure 5:
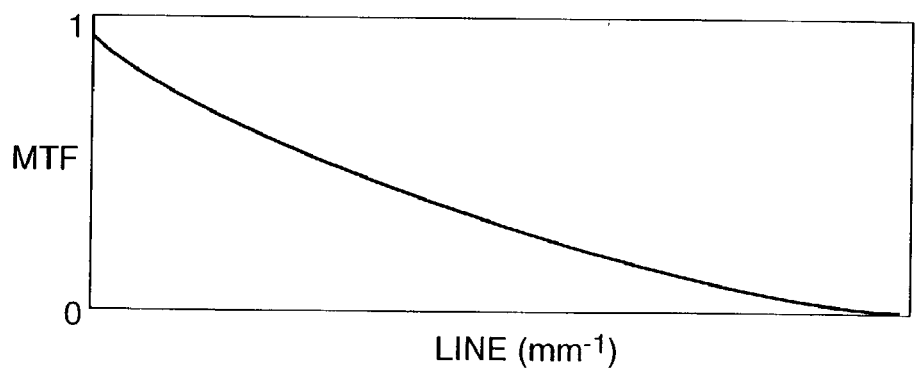
FIG. 5 is a graph showing space frequency characteristics, that is, MTF (Modulation Transfer Function), with the number of lines (Line) per 1 mm being in abscissa and MTF being in ordinate.

FIG. 5 is a graph showing space frequency characteristics, that is, MTF characteristics, with the number of lines (Line) per 1 mm being in abscissa and MTF being in ordinate. The definition analyzer 44 calculates MTF for image data of line-and-space patterns having mutually different number of lines and obtains the MTF characteristics data such as shown in FIG. 5. This MTF characteristics data becomes the definition data.

The definition evaluation device 45 is inputted with the definition data from the definition analyzer 44, compares the definition data with a preliminarily inputted reference data and judges whether or not the definition of the image of the reticle is within a predetermined reference range within which the performance of the reticle inspection apparatus can be guaranteed. The stage controller 47 is inputted with an output signal of the definition evaluation device 45 and corrects the position of the position sensor 33 by operating the sensor position regulating stage 34 when the definition of the image is out of the reference range. The input/output device 41 is connected to the image data generator 42 and the defect extractor 43, instructs the various devices of the controller system 40 and outputs an inspected result. Incidentally, the auto-focusing device in the reticle inspection apparatus according to this embodiment is constructed with the auto-focusing optical system 30, the auto-focusing controller 48 and the lens position controller 49 for regulating the position of the objective lens.

An operation of the reticle inspection apparatus according to this embodiment will be described, starting in the inspection of the reticle 16 by the inspection laser light 110 and the signal processing in this inspection. As shown in FIG. 2, the inspection laser light 110 emitted from the inspection light source 11 in direction −X is expanded by the telescope 12 and, after reflected to direction −Z by the mirror 13, transmits the beam splitter 20 and is condensed by the objective lens 14 to irradiate the reticle 16. In this case, the reticle 16 is irradiated with the inspection laser light 110 in the vicinity of a position on the reticle at which the diameter of the beam spot of the inspection laser light 110 becomes minimum. Incidentally, the auto-focusing operation for regulating the position of the reticle 16 such that the spot diameter of the inspection laser light 110 irradiating the reticle 16 becomes minimum will be described later.

The reticle 16 is mounted on the X-Y stage 17. The surface of the X-Y stage 17 on which the reticle 16 is mounted is substantially perpendicular to the optical axis 140 of the objective lens 14. The X-Y stage 17 responds to the signal from the X-Y stage controller 46 to move the reticle 16 thereon in X and Y directions. Therefore, the irradiating spot of the inspection laser light 110 on the reticle 16 is moved on the reticle 16 relatively. The X-Y stage controller 46 outputs the coordinates data of the X-Y stage 17 to the image data generator 42. A portion of the inspection laser light 110 condensed and irradiating the reticle 16, which is transmitted through the reticle 16 as a transmitted inspection light 111, is condensed on the inspection light sensor 19 by the lens 18 and its intensity is measured by the transmitted inspection light sensor 19. The other portion of the inspection laser light 110, which is reflected by the reticle 16 as a reflected inspection light 112, is deflected to direction −X by the beam splitter 20 and condensed on the reflected inspection light sensor 22 by the lens 21. Intensity of the reflected inspection light 112 is measured by the inspection sensor 22.

The light intensity signals obtained by the transmitted inspection light sensor 19 and the reflected inspection light sensor 22 are inputted to the image data generator 42. The image data generator 42 obtains light intensity distribution from an image data of the reticle 16 generated by processing the intensity signals from the transmitted inspection light sensor 19 and the reflected inspection light sensor 22 and the coordinates data of the reticle 16 from the X-Y stage controller 46. In the case where, for example, the line-and-space pattern shown in FIG. 3 is formed on the reticle 16, light intensity distribution of the image data of the reticle 16 becomes as shown in FIG. 4. The image data is outputted to the defect extractor 43 and the light intensity distribution data is outputted to the definition analyzer 44. The defect extractor 43 detects defect of the reticle 16 by comparing the image data with design data, etc., of the reticle 16. The image data of the reticle 16 and the defect data thus produced are outputted through the input/output device 41.

Next, an auto-focusing operation for maintaining the optimal distance between the reticle 16 and the objective lens 14 will be described. The auto-focusing laser light 310 emitted by the He—Ne laser 31 in direction −X is reflected by the mirror 32 to direction −Z and passes through a path, which is parallel to the optical axis 140 of the objective lens 14 and has an offset thereto. Thereafter, the auto-focusing laser beam 310 is transmitted through the mirror 13 and the beam splitter 20, condensed by the objective lens 14 and irradiates the reticle 16 obliquely with respect to the optical axis 140. The auto-focusing laser light 310 is reflected by the reticle 16 and transmitted through the objective lens 14 again as the reflected auto-focusing light 311, which travels in direction +Z through a path, which is in parallel to and separated from the optical axis 140. The reflected auto-focusing light 311 is transmitted through the beam splitter 20 and the mirror 13 and incident on the position sensor 33. The position sensor 33 detects the incident position of the reflected auto-focusing light 311.

In the reticle inspection apparatus according to this embodiment, the relation between the incident position of the reflected auto-focusing light 311 on the position sensor 33 and the position of the objective lens 14 with respect to the reticle is determined simply. That is, when the position of the objective lens 14 is optimal and the inspection laser light 110 is focused on the reticle 16, the reflected auto-focusing light 311 is incident on the position sensor 33 at a predetermined position. On the contrary, when the position of the reticle 16 is sifted in direction +Z or the position of the objective lens 14 is shifted in direction −Z, that is, when the position of the reticle 16 or the objective lens 14 is shifted in mutually approaching direction, the incident position of the reflected auto-focusing light 311 on the position sensor 33 is shifted in direction +X. On the other hand, when the position of the reticle 16 is shifted in direction −Z or the position of the objective lens 14 is shifted in direction +Z, that is, the reticle 16 and the objective lens 14 are shifted in mutually separating direction, the incident position of the reflected auto-focusing light 311 on the position sensor 33 is shifted in direction −X. Therefore, it is possible to determine whether or not the distance between the reticle 16 and the objective lens 14 is optimal by measuring the incident position of the reflected auto-focusing light 311 by the position sensor 33.

A signal from the position sensor 33, which is indicative of the incident position of the reflected auto-focusing light 311 on the position sensor, is processed in the auto-focusing controller 48. When the distance between the reticle 16 and the objective lens 14 is deviated from the optimal value, the auto-focusing controller 48 generates a signal for removing the deviation, which is outputted to the lens position controller 49 for regulating the position of the objective lens. The lens position controller 49 controls the operation of the lens position regulator 15 according to the input signal to regulate the position of the objective lens 14 such that the incident position of the reflected auto-focusing light 311 on the position sensor 33 becomes coincident with the predetermined position. Therefore, the position of the objective lens 14 is regulated such that the distance between the objective lens 14 and the reticle 16 is always kept constant.

As a result, the position of the reticle 16 is maintained in the vicinity of the minimum spot diameter of the inspection laser light 110.

Next, a diagnostic operation for diagnosing whether or not the relation between the incident position of the reflected auto-focusing light 311 on the position sensor 33 and the distance between the objective lens 14 and the reticle 16 is changed due to deformation, etc., of the reticle inspection apparatus to be caused by long term use thereof will be described. The definition analyzer 44 provides the definition data by processing the data of the light intensity distribution of the image data of the reticle 16 supplied by the image data generator 42. The definition data can be represented by MTF data obtained from various line-and-space patterns (see FIG. 3) on the reticle 16.

A producing method of definition data will be described. The light intensity distribution of the image data of the line-and-space pattern (see FIG. 3) outputted from the image data generator 42 is inputted to the definition analyzer 44. The light intensity distribution of the image data may be one shown in FIG. 4. The definition analyzer 44 obtains the maximum light intensity Imax and the minimum light intensity Imin of the intensity distribution shown in FIG. 4 and calculates MTF according to the equation (1). Further, the definition analyzer 44 obtains the period d of the line-and-space pattern (see FIG. 3) and calculates the number of lines per 1 mm (Line (mm$^{-1}$) according to the equation (2). The MTF characteristics data shown in FIG. 5 is obtained by the MTF and the number of lines per 1 mm. This characteristics data of MTF becomes the definition data.

Thereafter, the definition analyzer 44 (see FIG. 2) outputs the definition data to the definition judge device 45. The definition judge device 45 determines whether or not the definition data is within the tolerable range by comparing the definition data with the preliminarily set reference data. When the definition data is within the tolerable range, it is judged by the definition judge device that the auto-focusing device operates normally. On the other hand, when the definition data is out of the tolerable range, it is judged by the definition judge device that the auto-focusing device does not operate normally. The result of the judgement is stored in the definition judge device 45, etc., and is outputted to external devices through the input/output device 41. As described before, the diagnosis of the auto-focusing function of the reticle inspection apparatus is performed by judging whether or not the relation between the incident position of the reflected auto-focusing light 311 on the position sensor 33 and the distance between the objective lens 14 and the reticle 16 is changed from the initial setting.

Next, an automatic correcting operation of the reticle inspection apparatus will be described. The reticle inspection apparatus has a function of automatically correcting a change of the above mentioned relation between the incident position of the reflected auto-focusing light 311 on the position sensor 33 and the distance between the objective lens 14 and the reticle 16 by structural deformation, etc., of the reticle inspection apparatus by a long term use thereof. FIG. 6A and FIG. 6B shows the automatic correcting operation of the reticle inspection apparatus for automatically correcting the change of the relation between the incident position of the reflected auto-focusing light 311 on the position sensor 33 and the height of the objective lens 14, in which FIG. 6A illustrates a case where the relation is in the initially set state and the reticle inspection apparatus is normal and FIG. 6B illustrates a case where the relation is changed from the initial setting by structural deformation, etc., of the reticle inspection apparatus by a long term use thereof and the definition of image data becomes out of the tolerable range.

First, the case where the relation between the incident position of the reflected auto-focusing light on the position sensor 33 and the distance between the objective lens 14 and the reticle 16 is in the initial setting and the reticle inspection apparatus is normal will be described with reference to FIG. 6A. When the objective lens 14 is in a level or position 14a and the diameter of beam spot of the inspection laser light 110 on the reticle 16 is minimum, that is, when the inspection laser light 110 is focused on the reticle 16, the auto-focusing light 311a, which is the inspection laser light 110 reflected by the reticle 16, is incident on a position pa of the position sensor 33. This state is a reference state. When the position of the reticle 16 is shifted to direction +Z, the incident position of the reflected auto-focusing light 311a on the position sensor 33 is shifted to direction +X from the position pa and, when the position of the reticle 16 is shifted to direction −Z, the incident position of the reflected auto-focusing light 311a on the position sensor 33 is shifted to direction −X from the position pa. The shifting direction of the incident position of the reflected auto-focusing light 311a is detected by the position sensor 33 and the position of the objective lens 14 is automatically regulated according to the shift so that the inspection laser light 110 is always focused on the reticle 16.

However, when the position of the position sensor 33 is shifted to direction −X by a distance m due to structural deformation, etc., of the reticle inspection apparatus by a long term use thereof, the incident position of the reflected auto-focusing light 311b on the position sensor 33 is shifted to direction +X by a distance m relatively, as shown in FIG. 6B. Therefore, when the inspection laser light 310 is focused on the reticle 16, the incident position of the reflected auto-focusing light 311b, which is the auto-focusing laser light 310 reflected by the reticle 16, is shifted to a position pc. When looking from the position sensor 33, the position pc is deviated from the position pa shown in FIG. 6A to direction +X by the distance m.

On the other hand, the positions pa and pb on the position sensor 33 are the same when looked from the position sensor 33. As shown in FIG. 6B, when the incident position of the reflected auto-focusing light 311b is the position pc, the auto-focusing controller 48 considers such situation as the shift of the reticle 16 to direction +Z or the shift of the objective lens 14 to direction −Z and operates the lens position regulator 15 to regulate the position of the objective lens 14 to direction +X such that the incident position of the reflected auto-focusing light 311b becomes the position pb on the position sensor 33. As a result, the position of the objective lens 14 becomes the position or level 14b. With the objective lens 14 in the position 14b, the minimum spot of the inspection laser light 110 is not positioned on the reticle 16 and so the inspection laser light 110 is not focused on the reticle 16. Therefore, the definition of the image data of the reticle 16, which is produced by the image data generator 42 (see FIG. 2), is degraded.

As a result, when the definition analyzer 44 (see FIG. 2) produces the definition data of image data and outputs it to the definition judge device 45, the definition judge device 45 compares the definition data with the reference data and decides that the definition of image data is out of the tolerable range and outputs this decision to the sensor position regulating stage controller 47. The sensor position regulating stage controller 47 actuates the sensor position regulating stage 34 according to this decision to shift the position sensor 33 to direction +X by the distance m. The position of the position sensor 33 is returned to the position pa shown in FIG. 6A by this operation, so that the objective lens 14 is returned to the position 14a, resulting in that the minimum spot of the inspection light 110 is positioned on the reticle 16. In this manner, the positional shift of the position sensor 33 is automatically corrected and the normal auto-focusing function of the reticle inspection apparatus is maintained. Incidentally, the result of control of the sensor position regulating stage 34 is stored in the definition judge device 45, etc., and is outputted externally by the input/output device 41.

Since the reticle inspection apparatus according to this embodiment has the self diagnosis function for determining whether or not the auto-focusing function of the reticle inspection apparatus is working normally as mentioned above, it is possible to predict an occurrence of abnormality of the auto-focusing function before an erroneous inspection occurs. Further, since a maintenance timing of the reticle inspection apparatus can be predicted, it is possible to determine the timing of maintenance by preliminary negotiations with a user and to make preparations therefor. Therefore, it becomes possible to minimize a time period for which the reticle inspection apparatus is stopped for maintenance thereof.

Further, since the reticle inspection apparatus according to this embodiment has the automatic correcting function, it is possible to correct positional deviation of the position sensor 33 due to deformation, etc., of the structural components of the reticle inspection apparatus by a long time use thereof to thereby prevent focus shift from occurring for a long time period. Therefore, it is possible to reduce frequency of maintenance.

Figure 7:
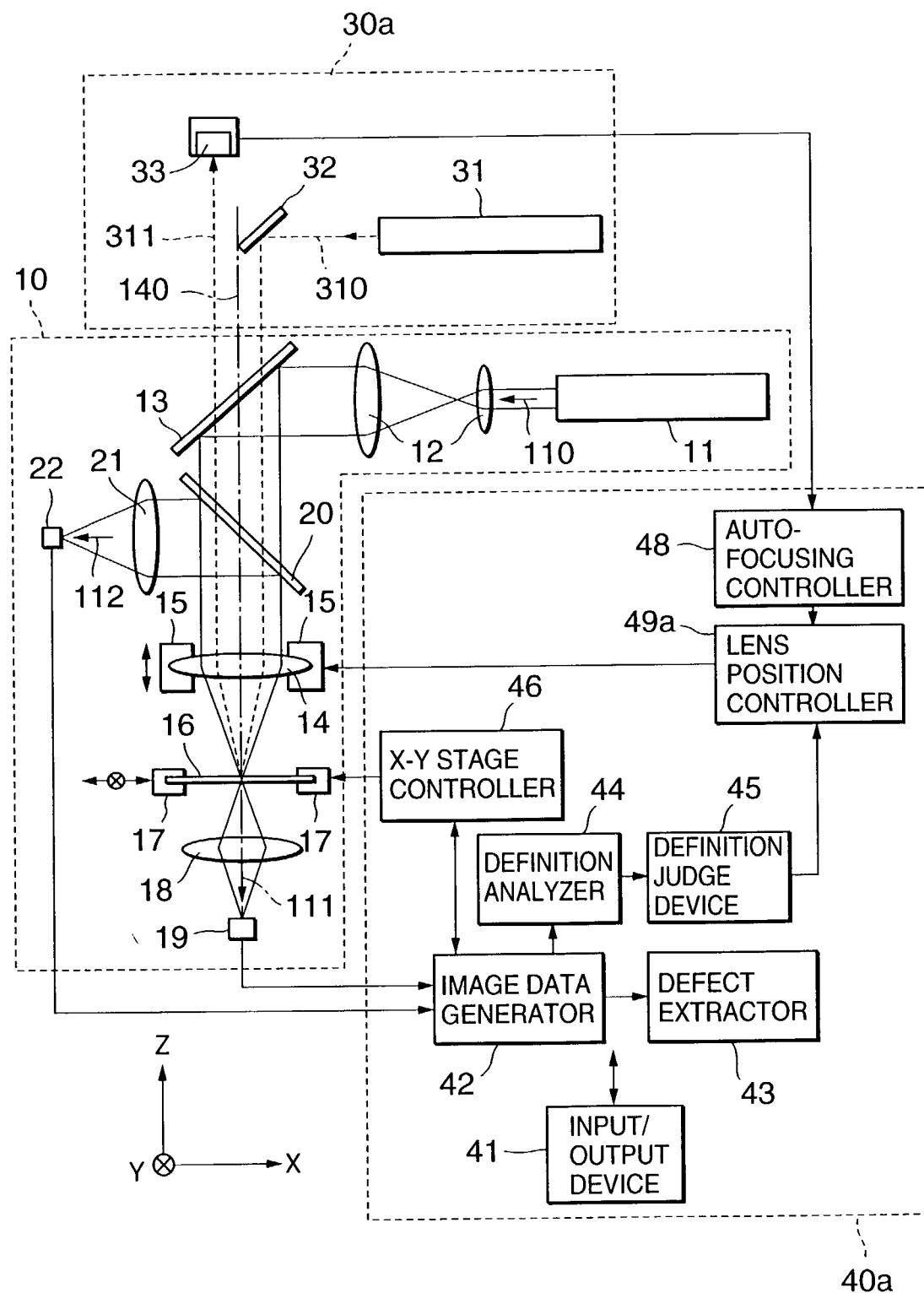
FIG. 7 is a block diagram showing a reticle inspection apparatus according to a second embodiment of the present invention.

Now, a second embodiment of the present invention will be described. FIG. 7 is a block diagram showing a reticle inspection apparatus according to the second embodiment of the present invention. Constructive components of this embodiment, which are the same as those of the reticle inspection apparatus according to the first embodiment (see FIG. 2) are depicted by the same reference numerals, respectively, without detailed description thereof. As shown in FIG. 7, the reticle inspection apparatus according to the second embodiment is constructed with an inspection optical system 10, an auto-focusing optical system 30a and a controller 40a. The inspection optical system 10 of the reticle inspection apparatus of this embodiment is identical to the inspection optical system 10 of the first embodiment. Further, the auto-focusing optical system 30a of the reticle inspection apparatus of the second embodiment is identical to the auto-focusing optical system 30 of the reticle inspection apparatus of the first embodiment, except that the sensor position regulating stage 34 (see FIG. 2) for regulating a position of the position sensor 33 is removed. Further, the controller system 40a of the reticle inspection apparatus of the second embodiment is identical to the controller system 40 of the first embodiment, except that the stage controller 47 (see FIG. 2) for controlling the stage 34 of the first embodiment is removed. Instead thereof, the second embodiment is constructed such that a judge signal from the definition judge device 45 is inputted to a lens position controller 49a for controlling position of an objective lens and the lens position controller 49a has a function of adding an offset to the position or level of the objective lens 14 on the basis of the judge signal from the definition judge device 45. Other construction of the reticle inspection apparatus according to the second embodiment are the same as those of the reticle inspection apparatus of the first embodiment.

An operation of the reticle inspection apparatus according to the second embodiment will be described. In the second embodiment, when the position of the position sensor 33 is shifted to direction −X by the distance m due to structural deformation, etc., of the reticle inspection apparatus, the position of the objective lens 14 is regulated to the position 14b as in the first embodiment if the initial setting of the auto-focusing control is unchanged, as shown in FIG. 6B. Since, therefore, the minimum spot of the inspection laser light 110 is not on the reticle 16, definition of image data is degraded. In such case, the definition judge device 45 judges the definition of image data as being out of the tolerable range and sends the judge signal to the objective lens position controller 49a. The objective lens position controller 49a adds an offset to the position of the objective lens 14 according to the judge signal and actuates the objective lens position regulator 15 such that the objective lens 14 is moved from the position 14b to the position 14a. Thus, the minimum spot of the inspection light 110 becomes on the reticle 16 again. The result of control of the objective lens position regulator 15 is stored in the definition judge device 45, etc., and outputted externally by the input/output device 41.

Figure 8:
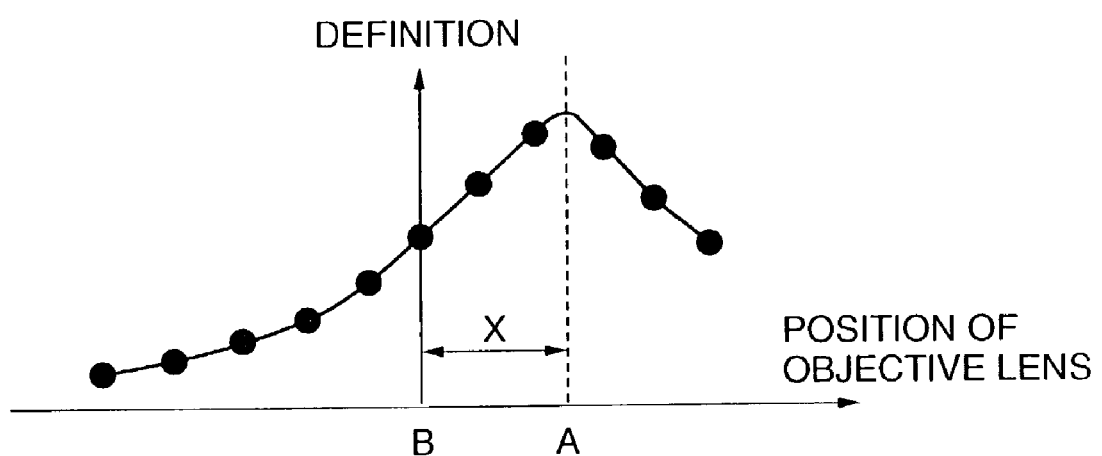
FIG. 8 is a graph showing a relation between a position of an objective lens with respect to a reticle and definition of a reticle image, with position of the objective lens being in abscissa and definition of the image data of the reticle being in ordinate.

Determination of the amount of offset to be added to the position of the objective lens 14 may be performed by the following method. FIG. 8 is a graph showing a relation between level or position of the objective lens and definition, with position of the objective lens 14 being in abscissa and definition of the image data of the reticle 16 being in ordinate. Patterns of the reticle 16 are measured at several vertical positions or levels of the objective lens 14 with using a level thereof corresponding to the auto-focusing position before correction as a center level and definition data in these levels of the objective lens 14. According to the definitions thus obtained, the relation between the position of the objective lens and the definition is obtained. This relation is shown in FIG. 8. In FIG. 8, a difference X between a position A of the objective lens at which the definition is highest and a position B thereof corresponding to the auto-focusing position before correction is the amount of offset.

The second embodiment differs from the first embodiment, in which the position sensor 33 is moved by the sensor position regulating stage 34 (see FIG. 2) to correct the level of the objective lens, in that the objective lens position controller 49a corrects the auto-focusing operation by adding the offset to the level of the objective lens 14. Therefore, even if the auto-focusing optical system gets out of order due to deformation, etc., of the constructive components, such functional disorder is automatically corrected. Therefore, the second embodiment can provide, in addition of the effect obtainable by the first embodiment, an effect that the structure of the reticle inspection apparatus can be simplified since the sensor position regulating stage 34 and the stage controller 47, which are indispensable for regulating the position of the position sensor 33 in the first embodiment, are removed.

In the second embodiment, the judge signal from the definition judge device 45 is inputted to the objective lens position controller 49a and the latter controller adds the offset to the level of the objective lens 14. However, it is possible to construct the reticle inspection apparatus such that the judge signal of the definition judge device 45 is inputted to the auto-focusing controller 48 and to give the function of adding an offset to the level of the objective lens 14 to the auto-focusing controller 48.

As described in detail hereinbefore, according to the present invention, it is possible to provide a reliable reticle inspection apparatus capable of automatically diagnosing an error of the auto-focusing function due to deformation of structural components thereof. Further, it is possible to provide a reticle inspection apparatus, which can automatically correct the error of the auto-focusing function thereof and can operates stably for a long period of time.

What is claimed is:

1. A reticle inspection apparatus comprising:
   an inspection laser light source for emitting an inspection laser light;
   an objective lens for condensing the inspection laser light and irradiating a reticle with the condensed inspection laser light;
   image generating means for generating an image of said reticle on the basis of the inspection laser light reflected by said reticle and the inspection laser light transmitted through said reticle and detecting said image of said reticle on defect therein;
   an auto-focusing laser light source for irradiating said reticle with an auto-focusing laser light in a direction obligue to an optical axis of said objective lens through said objective lens;
   a position sensor for detecting an incident position of the auto-focusing laser light reflected by said reticle and incident on said position sensor through said objective lens;
   lens position regulating means for calculating a distance between said objective lens and said reticle on the basis of an output signal of said position sensor and making a focal position of the inspection laser light coincident with an inspection position of said reticle by regulating a position of said objective lens according to the calculated distance; and
   definition judging means for analyzing definition of the image of said reticle and judging whether or not the definition is within a tolerable range, wherein said definition judging means judges whether or not the position of said position sensor is within a tolerable range by comparing a result of definition judgment performed by said definition judging means with a preliminarily set reference data.

2. A reticle inspection apparatus comprising:
   an inspection laser light source for emitting an inspection laser light;
   an objective lens for condensing the inspection laser light and irradiating a reticle with the condensed inspection laser light;
   image generating means for generating an image of said reticle on the basis of the inspection laser light reflected by said reticle and the inspection laser light transmitted through said reticle and detecting said image of said reticle on defect therein;
   an auto-focusing laser light source for irradiating said reticle with an auto-focusing laser light in a direction obligue to an optical axis of said objective lens through said objective lens;
   a position sensor for detecting an incident position of the auto-focusing laser light reflected by said reticle and incident on said position sensor through said objective lens;
   lens position regulating means for calculating a distance between said objective lens and said reticle on the basis of an output signal of said position sensor and making a focal position of the inspection laser light coincident with an inspection position of said reticle by regulating a position of said objective lens according to the calculated distance;
   definition judging means for analyzing definition of the image of said reticle and judging whether or not the definition is within a tolerable range; and position sensor regulating means for regulating a position of said position sensor on the basis of the result of definition judgment performed by said definition judging means.

3. A reticle inspection apparatus comprising:
   an inspection laser light source for emitting an inspection laser light;
   an objective lens for condensing the inspection laser light and irradiating a reticle with the condensed inspection laser light;
   image generating means for generating an image of said reticle on the basis of the inspection laser light reflected by said reticle and the inspection laser light transmitted through said reticle and detecting said image of said reticle on defect therein;
   an auto-focusing laser light source for irradiating said reticle with an auto-focusing laser light in a direction obligue to an optical axis of said objective lens through said objective lens;
   a position sensor for detecting an incident position of the auto-focusing laser light reflected by said reticle and incident on said position sensor through said objective lens;
   lens position regulating means for calculating a distance between said objective lens and said reticle on the basis of an output signal of said position sensor and making a focal position of the inspection laser light coincident with an inspection position of said reticle by regulating a position of said objective lens according to the calculated distance; and
   definition judging means for analyzing definition of the image of said reticle and judging whether or not the definition is within a tolerable range wherein the position of said objective lens is regulated by said lens position regulating means on the basis of the result of definition judgment performed by said definition judging means.

* * * * *